(12) United States Patent
Huang

(10) Patent No.: US 9,688,956 B2
(45) Date of Patent: Jun. 27, 2017

(54) METHOD FOR PRESERVING PROLIFERATION AND DIFFERENTIATION POTENTIAL OF MESENCHYMAL STEM CELLS

(71) Applicant: NATIONAL CHENG KUNG UNIVERSITY, Tainan (TW)

(72) Inventor: Lynn Ling-Huei Huang, Tainan (TW)

(73) Assignee: National Cheng Kung University, Taiwan (TW)

( * ) Notice: Subject to any disclaimer, the term of this patent is extended or adjusted under 35 U.S.C. 154(b) by 0 days.

(21) Appl. No.: 14/796,384

(22) Filed: Jul. 10, 2015

(65) Prior Publication Data

US 2015/0315542 A1    Nov. 5, 2015

Related U.S. Application Data

(63) Continuation-in-part of application No. 12/155,487, filed on Jun. 5, 2008, now abandoned.

(51) Int. Cl.
*C12N 5/00* (2006.01)
*C12N 5/071* (2010.01)
*C12N 5/0775* (2010.01)

(52) U.S. Cl.
CPC ......... *C12N 5/0602* (2013.01); *C12N 5/0667* (2013.01); *C12N 2533/70* (2013.01); *C12N 2533/72* (2013.01); *C12N 2533/74* (2013.01); *C12N 2533/78* (2013.01); *C12N 2533/80* (2013.01)

(58) Field of Classification Search
None
See application file for complete search history.

(56) References Cited

U.S. PATENT DOCUMENTS

| | | |
|---|---|---|
| 2002/0042132 A1 | 4/2002 | Gardner |
| 2005/0260753 A1 | 11/2005 | Shahar |
| 2008/0220526 A1 | 9/2008 | Ellison |

FOREIGN PATENT DOCUMENTS

| | | |
|---|---|---|
| WO | 98/50526 A1 | 11/1998 |
| WO | 2008/007082 A2 | 1/2008 |

OTHER PUBLICATIONS

C.B. Knudson, "Hyaluronan and CD44: strategic players for cell-matrix interactions during chondrogenesis and matrix assembly", Birth Defects Res. C. Embryo Today, 69: 174-196 (2003).
C.J. Sherr, "Cellular senescence: mitotic clock or culture shock?", Cell, 102:407-410 (2000).
D. Peck et al., "CD44 phosphorylation regulates melanoma cell and fibroblast migration on, but not attachment to, a hyaluronan substratum", Current Biology, 6(7) 884-890 (1996).
Lynn L.H. Huang-Lee et al., "Crosslinked-CNBr-activated hyaluronan-collagen matrices: effects on fibroblast contraction", (2002).
K.M. Safford et al., "Neurogenic differentiation of murine and human adipose-derived stromal cells", Biochem. and Biophys. Res. Communication, 294: 371-379, (2002).
L. Huang et al., "The effect of hyaluronan on osteoblast proliferation and differentiation in rat calvarial-derived cell cultures", J. Biomed. Mater Res. A, 66: 880-884 (2003).
Lynn L.H. Huang-Lee et al., "Crosslinked CNBr-activated hyaluronan-collagen matrices: effects on fibroblast contraction", Matrix Biology, 14: 147-157 (1994).
M. Stojkovic et al., "Effects on high concentrations of hyaluronan in culture medium on development and survival rates of fresh and frozen-thawed bovine embryos produced in vitro", Reproduction, 124: 141-153 (2002). 1-1.
R. Ogawa et al., "Adipogenic differentiation by adipose-derived stem cells harvested from GFP transgenic mice including relationship of sex differences", Biochem. and Biophys. Res. Communications 319: 511-517 (2004).
R. Ogawa et al., "Osteogenic and chondrogenic differentiation by adipose-derived stem cells harvested for GFP transgenic mice", Biochem. and Biophys. Res. Communications 313: 871-877 (2004).
S. Parrinello et al., "Oxygen sensitivity severely limits the replicative lifespan of murine fibroblasts", Nat. Cell Biol., 5(8): 741-747, (2003).
S.K. Nilsson et al, "Hyaluronan is synthesized by primitive hemopoietic cells, participates in their lodgment at the endosteum following transplantation, and is involved in the regulation of their proliferation and differentiation in vitro", Blood, 101(3), 856-862, (2013).
Takehiro Matsubara et al., "A new technique to expand human mesenchymal stem cells using basement membrane extracellular matrix", Biochem. and Biophys. Res. Communications, 313: 503-508, (2004).
Woodring E. Wright et al., "Telomere dynamic in cancer progression and prevention: fundamental differences in human and mouse telomere biology", Nat. Med., 6(8), 849-851, (2000).
Xuenong Zou et al., "Stimulation of porcine bone marrow stromal cells by hyaluronan, dexamethasone and rhBMP-2", Biomaterials, 25, 5375-5385 (2004).
Zuk et al., "Multilineage Cells from human adipose tissue: implications from cell-based therapies", Tissue Eng., 7(2), 211-228 (2001).

*Primary Examiner* — Blaine Lankford
(74) *Attorney, Agent, or Firm* — Michael Ye; Andrews Kurth Kenyon LLP

(57) ABSTRACT

A method for preserving proliferation and differentiation potential of undifferentiated cells, has steps of providing a culture carrier having a surface coated with a biological material selected from the group consisting of hyaluronan, chondroitin sulfate, carboxymethyl cellulose, carrageenan, alginate, and chitosan; and inoculating and culturing the undifferentiated cells on the surface in the culture carrier with an appropriate medium, such that the proliferation and differentiation potential of undifferentiated cells are preserved. The method can be used for expanding stem cells in vitro without loss of their replicative ability and differentiation capacity. Therefore, the method according to the present invention is amenable to application in regenerative medicine, tissue engineering, and therapy using umbilical cord blood and other cell sources such as peripheral blood, stem cells, tissue progenitor cells, and tissue cells.

12 Claims, 8 Drawing Sheets

METHOD FOR PRESERVING PROLIFERATION AND DIFFERENTIATION POTENTIAL OF MESENCHYMAL STEM CELLS

RELATED PATENT APPLICATION

This application is a continuation-in-part application and claims priority from subject matter disclosed in the earlier filed patent application Ser. No. 12/155,487, filed on Jun. 5, 2008, which is incorporated herein in its entirety by reference.

BACKGROUND OF THE INVENTION

1. Field of the Invention

This present invention relates to the field of cell biology of undifferentiated cells. More specifically, it relates to the propagation of undifferentiated cells, culture conditions and materials that facilitate propagation and use of undifferentiated cells.

2. Description of the Prior Arts

Undifferentiated cells, such as tissue progenitor cells, stem cells and the like, have great commercial potential in regenerative medicine or therapeutic tissue engineering. For the application of undifferentiated cells in regenerative medicine or therapeutic tissue engineering, a convenient method for culturing undifferentiated cells in an undifferentiated state in vitro is required.

Stem cells represent a generic group of undifferentiated cells and preserve the ability to renew themselves through cell division and can differentiate into different kinds of differentiated cells, and are found in all multiple cellular organisms. In mammals, three main of stem cells are embryonic stem cells that are found in blastocytes, extraembryonic stem cells are found in extraembryonic tissues, and postnatal stem cells that are found in postnatal tissues. The postnatal stem cells act as a repair system for replenishing specialized cells. As known in the field of the art, stem cells can propagate in culture in an undifferentiated state in the presence of feeder cells.

However, the potential risk of using feeder cells in the culture of the undifferentiated cells such as stem cells for regenerative medicine or therapeutic tissue engineering is that infectious agents such as viruses may infect the recipient. Therefore, there is a need for alternative method for culturing undifferentiated cells in vitro in an undifferentiated state in the absence of feeder cells.

Some of extracellular matrix components (ECM components) are used to replace the feeder cells for culturing undifferentiated cells to maintain them in an undifferentiated state. A few methods for culturing undifferentiated cells with ECM components such as laminin and collagen have been developed.

WO 98/50576 discloses a method of culturing neuroepithelial stem cells and oligodendrocyte-astrocyte precursor cells. It is observed that differentiation of the neuroepithelial stem cells into oligodendrocytes, astrocytes and neurons can be induced by replating the cells on laminin, withdrawing mitogens or adding dorsalizing agents to the growth medium.

WO 2008/007082 A2 discloses a method to maintain primate embryonic stem cells in cell culture conditions that are cell feeder free and serum free with a cell culture vessel coated with proteinaceous based cell culture support, wherein the proteinaceous based cell culture support is a collagen-based cell culture support.

Based on the foregoing, some ECM components are not only incapable of maintaining the differentiation potential of the cells, but induce the differentiation of the undifferentiated cells. It is suggested that the inconsistent effects of the different ECM components on the undifferentiated cells in culture result from the diverse properties of the different ECM components.

Hyaluronan (HA), one of the chief components of the extracellular matrix, is a non-sulfated glycosaminoglycan distributed widely throughout connective, epithelial, and neural tissues. HA is applied to postnatal stem cells and is reported to influence the cells on the migration, proliferation (S. K. Nilsson et al., (2003), *Blood*, 101: 856-862; D. Peck and C. M. Isacke, (1996), *Curr Biol*, 6: 884-890), and cell behavior (C. B. Knudson, (2003), *Birth Defects C Embryo Today*, 69:174-196) as well as the developmental capacity of bovine embryos in vitro (M. Stojkovic et al., (2002), *Reproduction*, 124: 141-153). The enhancement of osteogenic potential of rat osteoblasts by an initial administration of HA during first plating was also suggested (L. Huang et al., (2003), *J Biomed Mater Res A*, 66: 880-884). However, none of the above documents discloses that HA is able to maintain undifferentiated cells in culture, such as stem cells in an undifferentiated state.

In U.S. Pat. Application No. 20020042132, Gardner, David K. et al disclose a mammalian culture medium supplement comprising recombinant human albumin and fermented hyaluronan (HA) and a medium containing the supplement capable of increasing the viability of gametes or embryonic cells. Some other findings suggested that HA can stimulate the proliferation of primary porcine bone marrow stromal cells during early passage (X. Zou et al., (2004), *Biomaterials*, 25: 5375-5385). It is demonstrated that HA suspended in a medium stimulates rather than maintain proliferation capacity of cells.

Therefore the results from both the intrinsic difference between the proteinaceous ECM components and non-proteinaceous ECM components and the different means for introducing the ECM components to the undifferentiated cells are inconsistent.

New technology to manipulate the differentiation of undifferentiated cells, especially pluripotent stem cells would be a substantial achievement towards realizing the fall commercial potential of stem cell therapy, and will also be a very valuable means for medicine.

(a) SUMMARY OF THE INVENTION

Accordingly, applicants endeavored to develop a method for propagating stem cells in an undifferentiated state, and their use in preparing cells for regenerative medicine.

The main objective of the invention is to provide a method for preserving proliferation and differentiation potential of undifferentiated cells, having steps of providing a culture carrier having a surface coated with a non-proteinaceous extracellular matrix component; and inoculating and culturing the undifferentiated cells on the surface in the culture carrier with an appropriate medium, such that the proliferation and differentiation potential of undifferentiated cells are preserved.

The method according to the present invention can be used for expanding stem cells in vitro without loss of their replicative ability and differentiation capacity. Therefore, the method according to the present invention is amenable to the application in regenerative medicine, tissue engineering, and therapy using umbilical cord blood and other cell sources such as peripheral blood, stem cells, tissue progenitor cells, and tissue cells.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
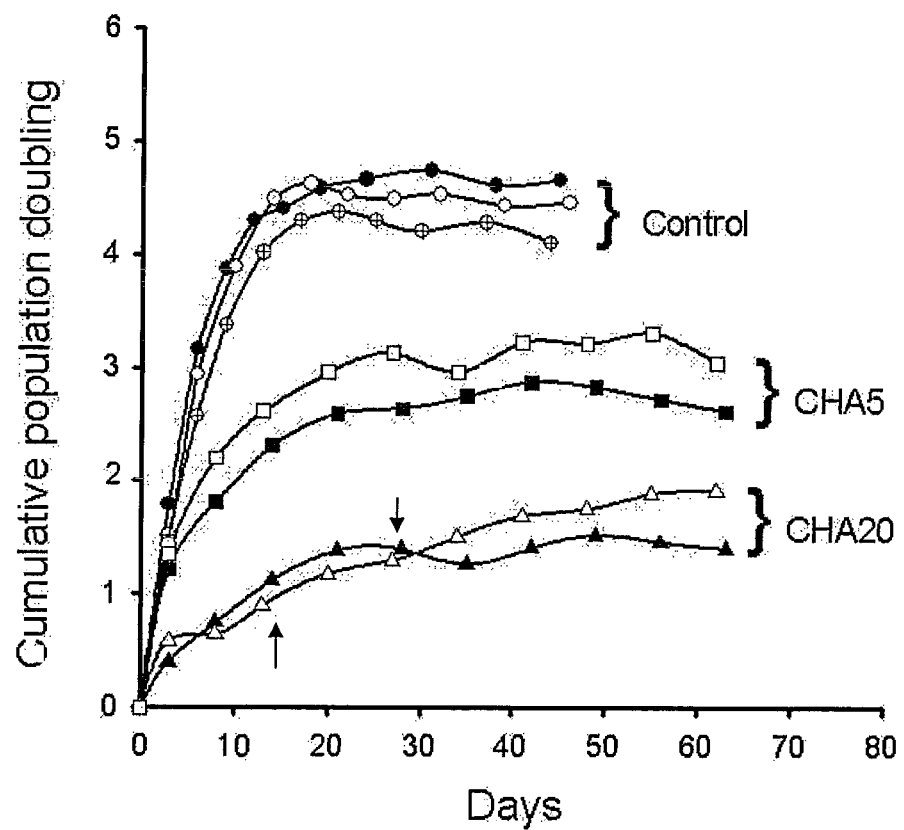
FIG. 1 illustrates proliferative lifespan of mADSCs (adipose-derived stromal cells from murine origin) cultured on control surface (regular tissue cultural surface), CHA5 and CHA20 (the regular tissue cultural surface was coated with 5 and 20 μg/cm² of HA)

The applicants aimed to assess the effects of HA on the feasibility of in vitro expansion and the preservation of differentiation capacity of long-term cultured undifferentiated cells; particularly, the stem cells; more particularly the mesenchymal cells; and more particularly adipose-derived stromal cell as well as placenta-derived mesenchymal stem cells.

Adipose-derived stromal cells (ADSCs) are shown to have differentiation capacity toward a variety of lineages in mammals (K. M. Safford et al., (2002), *Biochem Biophys Res Commun* 294: 371-379; R. Ogawa, et al., (2004), *Biochem Biophys Res Commun* 313: 871-877; R. Ogawa et al., (2004), *Biochem Biophys Res Commun* 319:511-517). For in vitro cultures, ADSCs especially mADSCs exhibit a finite proliferative capacity and acquire senescent morphology rapidly in applicants' preliminary studies. It is possible that murine stem cells are highly sensitive to environmental stresses, such as those induced by frequent subcultivation (C. J. Sherr and R. A. DePinho, (2000), *Cell* 102:407-410; W. E. Wright and J. W. Shay, (2000), *Nat Med*, 6: 849-851) or the hyperoxic condition in vitro (S. Parrinello et al., (2003), *Nat Cell Biol* 5: 741-747). This may result in impaired differentiation capability similar to subcultured mesenchymal stem cells reported (T. Matsubara et al., (2004), *Biochem Biophys Res Commun* 313: 503-508). For a long-term culture, mADSCs at latter passages demonstrated a marked decline in proliferative activity, exhibited senescent morphology and reduced differentiation potentials, particularly osteogenesis. To extend the lifespan of mADSCs, culture conditions containing hyaluronan (HA) were examined in the following examples, a culture condition where HA was pre-coated on the cultural surface (CHA) suggested that HA is useful for preserving the proliferation and differentiation potentials of long-term cultured mADSCs.

In another aspect, the proliferative activity of placenta-derived mesenchymal stem cells (PDMSCs) at latter passages for long-term culture was also examined in the following examples.

The following definitions and methods are provided to better define the present invention and to guide those with ordinary skill in the art in the practice of the present invention. Unless otherwise noted, terms are to be understood according to conventional usage by those with ordinary skill in the relevant art.

One aspect of the present invention provides a method for preserving proliferation and differentiation potential of undifferentiated cells, comprising steps of: providing a culture carrier having a surface coated with a biological material selected from the group consisting of polysaccharide, and sulfated polysaccharide; and inoculating and culturing the undifferentiated cells on the surface in the culture carrier with an appropriate medium, such that the proliferation and differentiation potential of undifferentiated cells are preserved.

The term "preserving" as used herein refers to maintaining, conserving, saving, upholding, keeping, continuing, carrying on or sustaining such that the proliferation rate of cells may be slowing down decreasing or delaying to simulate the in vivo dormant state. Postnatal stem cells in vivo are usually at a "dormant state", a slow cell-cycling phenomenon, and proliferate when prompted by tissue-regeneration or -repair signaling. The present invention may hold undifferentiated cells at a slow-cycling status in vitro, which may simulate the in vivo condition to keep cells in the primitive state so as to preserve the proliferation and differentiation potential of cells.

The term "differentiation" as used herein refers to a process by which descendants of a single cell produce morphological and functional specializations.

The term "differentiation potential" as used herein refers to being potent to undergo differentiation.

According to the present invention, the undifferentiated cells are obtained from a mammal such as bovine, porcine, murine, equine, canine, feline, ovine, simian, and human. More particularly, the undifferentiated cells are obtained from human or murine.

According to the present invention, the undifferentiated cells are selected from the group consisting of stem cells, tissue progenitor cells and mesenchymal cells. Preferably, the undifferentiated cells are mesenchymal cells. More preferably, the undifferentiated cells are selected from the group consisting of adipose-derived stromal cells, placenta-derived stem cells and bone marrow-derived stem cells. More preferably, the undifferentiated cells are adipose-derived stromal cells. Most preferably, the undifferentiated cells are placenta-derived stems cells.

The term "culture carrier" as used herein refers to an element that can serve as a carrier or support during cell culture, and this term should not be construed in any limiting way.

According to the present invention, "culture carrier" should be understood as including, but not limited to, conventional culture vessels such as stirring flasks, stirred tank reactors, petri dishes, multiwell plates, microtiter plates, test tubes and culture flasks, cover glass, or the like. Such culture carriers are preferably formed of materials including, for example, polystyrene, polypropylene, acrylate polymers, nylon, nitrocellulose, sepharose, and so forth.

According to the present invention, the biological material are polysaccharide and sulfated polysaccharide. More preferably, the biological material is selected from the group consisting of glycosaminoglycan, sulfated glycosaminoglycan and derivatives thereof.

More preferably, the biological material is selected from the group consisting of hyaluronan, chondroitin sulfate, carboxymethyl cellulose, carrageenan, alginate, and chitosan.

Most preferably, the biological material is selected from the group consisting of hyaluronan and derivatives thereof.

As used herein, hyaluronan (also known as hyaluronic acid or hyaluronate) is a naturally occurring polymer of repeated disaccharide units of N-acetylglucosamine and D-glucuronic acid.

The hyaluronan derivatives are hyaluronic acid esters, crosslinked compounds of hyaluronic acid, hemiesters of succinic acid or heavy metal salts of the hemiester of succinic acid with hyaluronic acid or partial or total esters of hyaluronic acid, sulphated hyaluronic acid, N-sulphated hyaluronic acid or the derivatives thereof.

More preferably, a hyaluronan derivative is produced through a cyanogen bromide activation procedure according to the publication of (Lynn L. H. Huang-Lee and Marcel E. Nimni 1994. Crosslinked cyanogen bromide activated hyaluronan-collagen matrices: effects on fibroblast contraction. *Matrix Biology,* 14: 147-157).

According to the present invention, the appropriate medium is any known culture medium in the field of the art that is suitable for culturing undifferentiated cells according to the present invention. For example, the appropriate medium may include, but not limited to, Dulbecco's modified Eagle's medium (DMEM), Eagle's minimal essential medium, RPMI, Medial 99, F-12 medium, William's medium E or the like. Preferably, the appropriate medium is any of the aforesaid culture medium supplemented with fetal bovine serum or the like.

According to the present invention, upon CHA treatment, mADSCs tended to form cell aggregates with gradual growth profiles. After transferring mADSCs from CHA to control surface, they were shown to have an extended lifespan and an increase of osteogenic potential. Therefore, in another aspect of the present invention, the method according to the present invention can further comprises subculturing the undifferentiated cells in a second culture carrier. Preferably, the second culture carrier has a surface that is coated with the biological material. In yet another aspect of the present invention, the appropriate medium is essentially free of the biological material whereby the proliferation and differentiation potential of the undifferentiated cell can both be preserved.

The terms "coating" and "coated" as used herein refer to applying a biological material to a surface of the culture carrier by known methods in the field of the art, for example, but not limited to, an application method, an immersion method or the like.

The application method includes applying a biological material in solution to a surface of a culture carrier, optionally, washing the surface with water and optionally, drying the surface.

The immersion method includes adhering a biological material layer to a surface of the culture carrier by immersing the culture carrier in an aqueous solution of thebiological material, and optionally, washing the surface with water and then drying the surface. A concentration of the biological material in solution used for these methods is not limited.

Particularly, methods disclosed in U.S. Pat. No. 6,129,956 for coating the surfaces of objects with hyaluronic acid, derivatives thereof or other natural or semisynthetic polymers can be utilized in the present invention for preparing a culture carrier having a surface coated with a non-proteinaceous extracellular matrix component.

According to the present invention, the surface of the culture carrier coated with the biological material is prepared by a method comprising steps of: coating a surface of the culture carrier with a coating composition containing about 1 ng/mL to about 1 g/mL of the biological material; optionally incubating the coating composition on the surface of the culture carrier; and drying the culture carrier with the coating composition thereon.

According to the present invention, the coating composition containing about 1 ng/mL to about 1 g/mL of the biological material is prepared by dissolving the biological material in an appropriate solvent. Particularly, the appropriate solvent is an aqueous solvent, such as water, saline or the like.

Preferably, in the coating step the surface is coated with the biological material in an amount from about 1 $\mu g/cm^2$ to 200 $\mu g/cm^2$; more preferably, about 1 $\mu g/cm^2$ to 100 $\mu g/cm^2$; more preferably, about 5 $\mu g/cm^2$ to 100 $\mu g/cm^2$. Most preferably, about 30 gig/cm².

According to the present invention, the biological material has an average molecular weight in a range from 1 KDa to 20,000 KDa; and preferably in a range from 10 KDa to 15,000 KDa. The present invention may be employed for application in regenerative medicine, tissue-engineering, therapy using umbilical cord blood or the like for treating various target diseases. The target diseases are, for example, but not limited to, malignant tumor (such as leukemia, lymphoma or the like), genetic disease (such as cardiac disease or the like), autoimmune disease (such as multiple sclerosis, rheumatoid arthritis or the like) or tissue/organ loss (such as defects in skin, bone, cartilage, liver, neuron, brain, cornea, vessel, stomach, intestine, colon, sclera or the like).

Another aspect of the present invention provides a method for using a culture carrier having a surface coated with a biological material selected from the group consisting of polysaccharide, sulfated polysaccharide and derivatives thereof to preserve the proliferation and differentiation potential of undifferentiated cells.

According to the present invention, the surface is coated with the biological material in an amount from about 1 $\mu g/cm^2$ to 200 $\mu g/cm^2$.

In examples below, abbreviations further defined have following meanings. Abbreviations not defined have their generally accepted meanings, or meanings as defined above.

EXAMPLES

Example 1

Altered Proliferative Behaviors of mADSCs in Response to HA

Materials and Methods:

1. Isolation and Culture of mADSCs mADSCs were isolated as previously described (R. Ogawa, et al., (2004), Supra.). Male FVB/N mice were housed and raised at National Cheng Kung University in Taiwan under standard conditions according to institutional guidelines for animal regulation. Briefly, inguinal fat pads from FVB/N mice were harvested and washed with phosphate buffered saline (GibcoBRL, Grand Island, USA) and were then finely minced and digested with 0.1% collagenase (Worthington, Lakewood, USA) at 37° C. for 45 minutes. An equal volume of Dulbecco's modified Eagle's medium (DMEM, GibcoBRL) containing 10% fetal bovine serum (FBS, Biological Industries, Israel) (hereafter referred to DMEM-10% FBS) was added and the resulting solution was filtered through a 100-μm mesh, followed by centrifugation at 250×g for 10 minutes. The pellet was collected and resuspended in 160 mM $NH_4Cl$ (Sigma, USA) to lyse the red blood cells and centrifuged at 250×g for 10 minutes. The cell pellet was collected and resuspended in a conventional culture medium of DMEM-10% FBS containing 1% antibiotic/antimycotic solution or the same in addition of indicated HA-containing medium. The cell suspensions were then plated at $1 \times 10^4$ cells/$cm^2$ on a regular culture surface or on HA pre-coated surface and incubated at 37° C. with 5% $CO_2$.

2. mADSCs Cultured in Regular and HA-Containing Culture Conditions mADSCs cultured with DMEM-10% FBS on regular culture surface were used as the control. A HA-containing culture condition was applied, wherein a HA pre-coated surface was prepared by coating HA on a regular culture surface and used as CHA culture system. For preparing culture system with 20 μg/$cm^2$ HA (CHA20), 500 μL of 4 mg/mL hyaluronan solution was evenly applied to a well of a 24-well plate (Nunc Cat. No. 142475) which was positioned horizontally and prewarmed between 40° C. to 50° C. 300 μL and 190.5 μL of HA solution were respectively aspirated sequentially leaving about 5 μL/$cm^2$ HA solution in each well of the 24-well plate. The culture system with 5 μg/$cm^2$ HA (CHA5) was prepared in accordance with the aforesaid except the concentration of the hyaluronan solution was proportionally reduced. The plate was desiccated by heating and sterilized by ozone for 1 hour. The state of HA coating in the 24-well plate was further assured by staining with 1% w/v alcian blue in 3% w/v acetic acid. The plate was stored in a desiccator for later use within a period of time not exceeding one week.

mADSCs cultured with DMEM-10% FBS on regular culture surface were used as control. CHA represents that mADSCs were cultivated with DMEM-10% FBS on HA pre-coated surfaces containing 5 μg/$cm^2$ (CHA5) or 20 μg/$cm^2$ (CHA20) of HA. Serial passages of mADSCs cultured in control and CHA were carried out when cells reached confluence. mADSCs were trypsinized, centrifuged and resuspended in appropriate culture medium, DMEM-10%/FBS for control and CHA groups. The mADSCs were then plated at $1 \times 10^4$ cells/$cm^2$ in each group. The increase of population doubling (ΔPD) was calculated according to the formula of ΔPD=log $(N_f/N_0)$/log 2, where $N_f$ is the final number of cells at subconfluence, and No is the initial number of plated cells.

3. Transfer Culture mADSCs initially cultured on CHA20 for 3 and 5 passages were subcultured into regular culture surfaces. The term "CHA_P3/C" and "CHA_P5/C" denotes the transfer culture and subculture of mADSCs from CHA20 at P3 (passage 3) and at P5 (passage 5) respectively to the regular culture surface. "P3+X" denotes that mADSCs were cultured on CHA20 for three passages and then cultured on regular culture surface for "X" passages. ΔPD was calculated as above.

4. Induction of Cell Differentiation

Osteogenic induction of mADSCs were carried out according to the procedures reported by Zuk et al., (2001), Tissue Eng, 7:211-228 with minor modifications. For differentiation, mADSCs at each passage, and under HA-containing culture systems (i.e. CHA) as described in "2. mADSCs cultured in regular culture conditions and CHA culture system" were initially plated at $1 \times 10^4$/$cm^2$ and cultured for 3 days prior to induction. For osteogenic induction, mADSCs were cultured in DMEM-10% FBS supplemented with 10 μg/mL insulin, 10 mM β-glycerophosphate, 100 nM dexamethasone, and 50 μg/mL ascorbic acid-2-phosphate for at least 2 weeks. For quantifying the degree of osteogenesis, the cells were fixed and stained with silver nitrate. The calcium deposition regions were shown in black and ten microscopic fields therefrom were assessed and calculated by Sigma Scan Pro (SPSS Inc.) for each triplicate sample.

5. Statistical Analysis

Student's t test was used to calculate p values.

Experiments:

I. Morphology Change of mADSCs in Response to HA mADSCs were harvested and cultured under HA-containing culture conditions (CHA) or control culture system for one passage (P1) and five passages (P5) as described above. Cell morphology of mADSCs was examined at the first passage (P1) and the fifth passage (P5) respectively.

II. Proliferative Lifespan of mADSCs in Response to HA

Proliferative lifespan of mADSCs cultured on control and CHA (5 and 20 μg/$cm_2$) was ascertained by the increase of population doubling respectively as described above. Three independent experiments were performed in control group, while two independent experiments were performed in each of CHA5 and CHA20 group.

III. Prolongation of Lifespan after Preculturing on CHA

The mADSCs were initially cultured on CHA20 for 3 and 5 passages, and then transferred to control surface for subsequent cultures. The cumulative population doublings of mADSCs after transferring to control surface were calculated and plotted versus time with each dot representative of one passage. Three independent experiments were carried out in CHA_P3/C while two were carried out in CHA_P5/C.

IV. Preservation of Osteogenic Potential after Pre-Conditioning with HA

The mADSCs cultured on control and CHA20 for 5 passages and the mADSCs derived from CHA_P3/C at 7th passages (P3+7) were incubated with osteogenic induction medium for 14 days. The cells were then fixed and the extent of matrix calcification was examined by silver nitrate staining where the calcium deposition region is shown in black. The extent of osteogenesis was quantified by scanning the $AgNO_3$ positive area as described above.

Results:

I. Morphology Change of mADSCs in Response to HA

Administration of HA (CHA) for culturing mADSCs exhibited altered proliferative behaviors. The mADSCs cultured on CHA tended to form cell aggregates even through latter passages (P5), whereas mADSCs cultured with suspended HA spread well on the culture surface. Interestingly, fewer cells at P5 were found morphologically senescent in CHA groups in comparison to the control group.

II. Proliferative Lifespan of mADSCs in Response to HA

A comparison of the proliferative lifespans of mADSCs in different conditions was shown in FIG. 1. Upon culturing on CHA5 and CHA20, mADSCs exhibited a much more gradual growth profile and almost no increase in cell numbers at each passage after P5. In addition, the doubling of cell numbers or the turnover of cell-cycling seemed to be slower with increasing amount of CHA (CHA20 versus CHA5).

III. Prolongation of Lifespan after Preculturing on CHA

Figure 2:
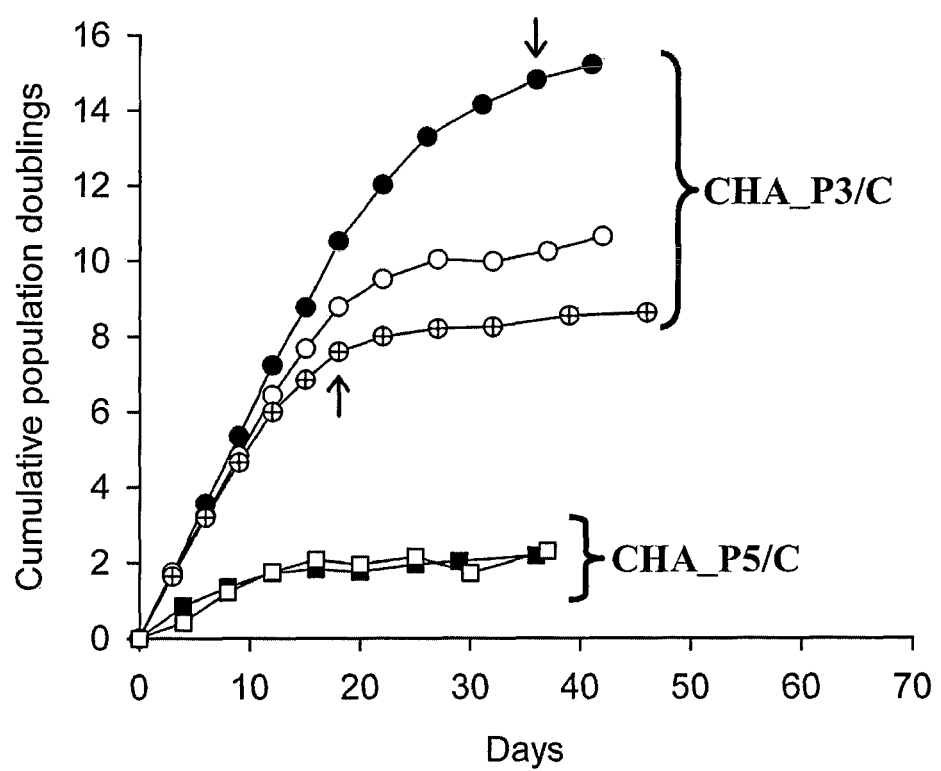
FIG. 2 illustrates proliferative lifespan of mADSCs thereafter in response to transfer culture from CHA20 to control surface.

To further elucidate the effects of CHA, mADSCs initially cultured on CHA20 for three and five passages (indicated by arrows in FIG. 1) were then transferred to regular culture surface and subcultured for passages. The morphology of mADSCs after transferring remained fibroblastic for at least 5 passages (P3+5), with some cells being larger and flatter at P3+7 (data not shown). A higher ΔPD was observed in CHA_P3/C groups, while the cells failed to proliferate in CHA_P5/C groups (FIG. 2). Lifespan of mADSCs in CHA_P3/C groups was shown to extend between 6 to 10 passages (FIG. 2, up and down arrows). For example, in one experiment, the lifespan of the mADSCs extended to 10 passages, i.e. 36 days (arrow down), while in another experiment, the lifespan extended to only about 6 passages, i.e. 18 days (arrow up).

IV. Preservation of Osteogenic Potential after Pre-Conditioning with HA

Figure 3:
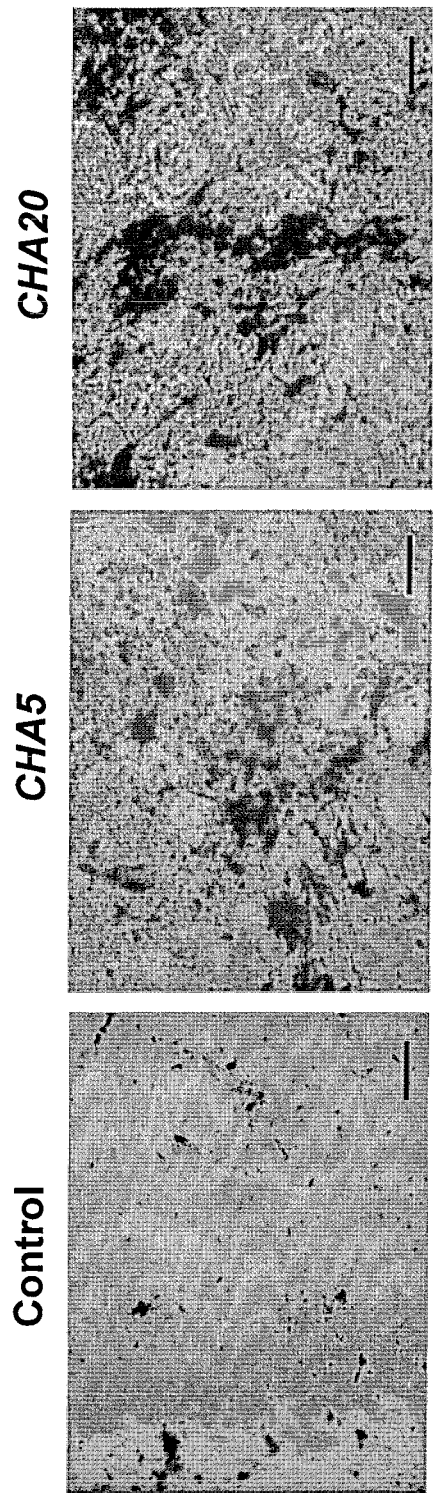
FIG. 3 illustrates osteogenic potentials of mADSCs at passage 5 from control, CHA5 and CHA20 surfaces.
Figure 4:
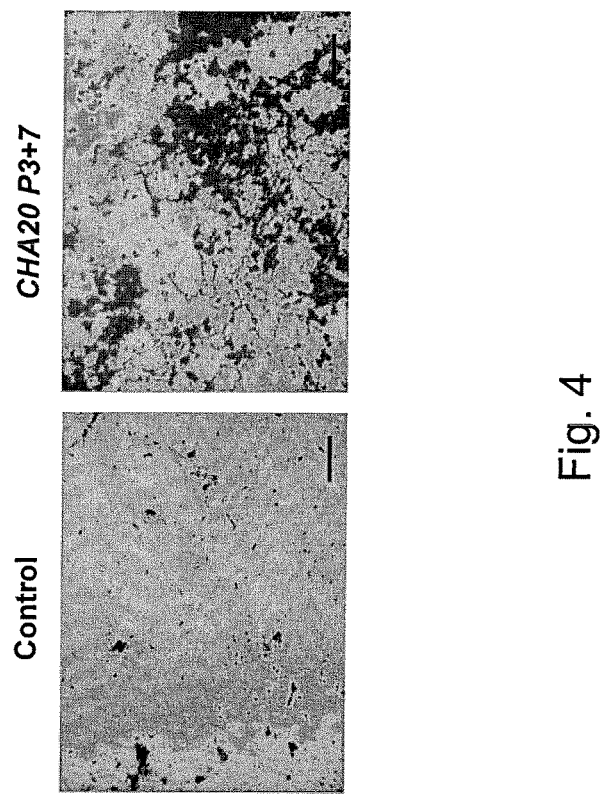
FIG. 4 illustrates osteogenic potentials of mADSCs from control (mADSCs at passage 5) and CHA20 P3+7 (mADSCs were initially cultured on CHA 20 for three passages and then transferred to the regular tissue cultural surface for another 7 passages)

The mADSCs that underwent various HA treatments for 1 and 5 passages were subjected to osteogenic induction as described above. During differentiation at P5, mADSCs of the CHA groups deposited sufficient amounts of calcium visible in black after silver nitrate staining on day 7 post-induction (as shown in FIG. 3, bar represents 100 μm). The osteogenic potential of transferred mADSCs which was pre-incubated with CHA20 (CHA20_P3/C) was also enhanced even at P3+7 (FIG. 4). From the results, mADSCs pre-conditioned by transfer culture of CHA_P3/C demonstrated a preservation of osteogenic potential at (P3) (FIG. 4) and latter passage (P5) (data not shown) and the differences between HA pre-conditioned groups and control group were shown to be significant ($p<0.01$ at least).

Example 2

Altered Proliferative Behaviors of hPDMSCs in Response to HA

Materials and Methods:

1. Isolation and Culture of Human Placenta-Derived Mesenchymal Stem Cells (hPDMSCs)

Third trimester (38 to 40 weeks GA, n>10) placenta tissue were collected after Cesarean sections of healthy human donor mothers. Specimen was obtained after informed consent and all experiments were approved by the local institutional review board. After amnion and decidua were manually separated, chorionic villi from the fetal part were minced, and then degraded with collagenase (200 U/mL, Sigma) for 30 minutes at 37° C. in water bath by gently orbital shaking. Through Percoll gradient (Pharmacia Biotech) centrifugation (density=1.073 g/cm$^3$), mononuclear cells were purified and propagated at $2\times10^4$ cells/cm$^2$ in complete medium, i.e. Dulbecco's modified Eagle's medium-low glucose (DMEM-LG, Invitrogen) containing 10% fetal bovine serum (Biological Industries), and 100 unit/mL gentamycin (Biological Industries). Cells were incubated at 37° C. in an atmosphere of 5% $CO_2$. At 14 days after initial plating, colonies were harvested and passaged for expansion on regular culture surface.

2. hPDMSCs Cultured in Regular and HA-Containing Culture Conditions

HA solution was prepared by dissolving HA powder (M.W.=$1\times10^6$ Da, Genzyme) in ddH$_2$O, then aliquoted and stored at −80° C. CHA3 were prepared by directly coating HA (Huang-Lee and Nimni, (1994), Matrix Biol. 14: 147-57) on regular culture surface, then dried on hot plate at 45° C. for at least 30 minutes, wherein number represents number of micrograms per square centimeter of HA coating (being 3 μg/cm$^2$ in this example). The efficacy of HA coating was evaluated by alcian blue staining. Before using CHA as culture system for hPDMSCs, CHA culture system was sterilized by ozone gas.

3. Continuous Passage of hPDMSCs hPDMSCs formed symmetric colonies at 14 day after initial plating, were harvested, then separated into two parts for propagation on regular culture surface and CHA, respectively. Thereafter, cells were passaged in 3-day intervals for 3 weeks. The cell numbers were determined every passage by hemacytometer.

4. Measurement of Proliferative Rate

At passage 4, hPDMSCs in exponential growth phase were trypsinized from regular culture surface to generate single-cell suspension and replated on regular culture surface or various CHA at $1\times10^4$ cells/cm$^2$ cell density, then incubated at 37° C. for the following 6 days culture period. Cell numbers were counted with hemacytometer every 24 hrs for 6 consecutive days, and cell growth curve was plotted based on these results.

5. Statistical Analysis

All data were reported as means and standard deviations of means obtained from the results of the triplicates. Statistical comparisons were made by one-way analysis of variance (ANOVA) for unpaired samples and differences with p value less than 0.05 was regarded as significant.

Experiments:

I. Proliferative Properties of hPDMSCs in Long-Term Cultivation on CHA Culture System The efficacy of HA coating was evaluated by alcian blue staining, HA was found to form a thin layer covering the regular culture surface when the surface contained 3 μg/cm$^2$ HA or more (data not shown). Therefore, CHA3 was chosen as cultural system to compare with regular culture surface (as Control) on hPDMSCs proliferation. hPDMSCs were seeded at $1\times10^4$ cells/cm$^2$ density, and then followed by 6 days culture period.

The proliferative activity of hPDMSCs was evaluated through serial passage in Control or CHA3 culture system. The total colonies of hPDMSCs from primary culture were harvested, and then separated into two parts for propagation in Control and CHA3. The increase of population doubling (ΔPD) was calculated as described above.

Figure 5:
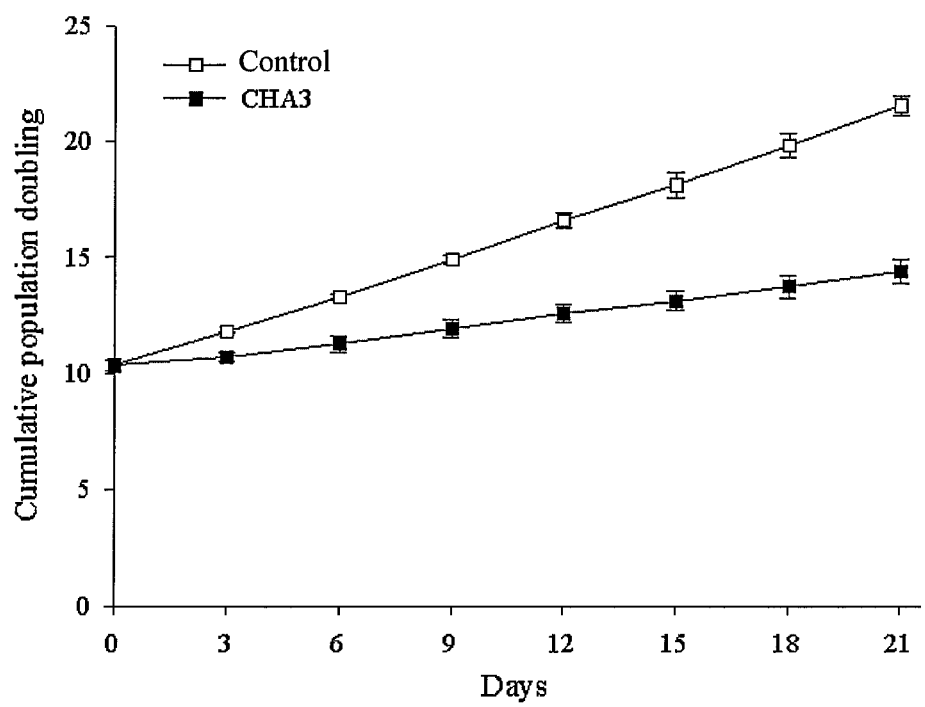
FIG. 5 illustrates consistently slow proliferation of hPDMSCs (placenta derived mesenchymal stem cells from human origin) on CHA3 (the regular tissue cultural surface was coated with 3 μg/cm² of HA) in long-term cultivation.

Results:

I. Proliferative Properties of hPDMSCs not Impeded by CHA in Long-Term Cultivation The cumulative population doubling of hPDMSCs in the beginning of this experiment was about 10. During the culture period of 3 weeks, the cumulative population doublings were measured by cell counting and illustrated in FIG. 5. The constant increase of cell number of hPDMSCs grown on CHA3 implied that these cells maintained the proliferative property.

Example 3

Altered Proliferative Behaviors of Undifferentiated Cells in Response to Biological Materials Materials and Methods:

Biological materials hyaluronan (HA), chondroitin sulfate (S), carboxymethyl cellulose (M), carrageenan (G), and alginate (A) were coated at 1 µg/cm$^2$, 5 µg/cm$^2$, 30 µg/cm$^2$, 100 µg/cm$^2$, and 200 µg/cm$^2$ respectively on tissue cultural surface (referred as control group). Specifically, hyaluronan (HA), chondroitin sulfate (S), carboxymethyl cellulose (M), carrageenan (G), and alginate (A) were coated at 30 µg/cm$^2$. The various surfaces were dried and sterilized. In preferable embodiment, the above various polysaccharides or sulfated polysaccharides (hyaluronan, chondroitin sulfate, carboxymethyl cellulose, carrageenan, and alginate) at high concentrations about 0.001 mg/ml, 0.01 mg/ml, 0.1 mg/ml, 1 mg/ml, 10 mg/ml, 100 mg/ml were respectively added to the cultural media.

Undifferentiated cells fibroblasts, perichondral progenitor cells (PCPC), adipose derived stromal cells (ADSC) and placenta derived mesenchymal stem cells (PDMSC) were respectively cultured on the various surfaces or various media for certain passages. In order to prove that the above polysaccharides, sulfated polysaccharides and derivatives thereof can preserve the proliferation and differentiation potentials of undifferentiated cells, the above cells preconditioned on the various surfaces or various media for certain passages were transferred to a regular tissue cultural surface respectively and the differentiation potentials of osteogenesis, chondrogenesis, adipogenesis were studied.

TABLE 1

The maintenance of proliferation and differentiation potentials of the indicated cells preconditioned on the various surfaces or various media.

| | | Polysaccharides | | | | | |
|---|---|---|---|---|---|---|---|
| Cell type | TCS | HA | S | M | G | A | C |
| fibroblasts | − | + | + | + | + | + | + |
| PCPC | − | + | + | + | + | + | + |
| ADSC | − | + | + | + | + | + | + |
| PDMSC | − | + | + | + | + | + | + |

"−" indicates a negative effect.
"+" indicates a positive effect.

TABLE 2

Differentiation potentials of cells cultured at indicated conditions.

| | Adipogenesis | Osteogenesis | Chondrogenesis |
|---|---|---|---|
| P3* TCS | ++ | ++ | ++ |
| P20* TCS | −− | −− | −− |
| P1 + 18 + 1 S to TCS** | +− | +− | +− |

TABLE 2-continued

Differentiation potentials of cells cultured at indicated conditions.

| | Adipogenesis | Osteogenesis | Chondrogenesis |
|---|---|---|---|
| P1 + 18 + 1 C to TCS*** | ++ | ++ | +− |

1. *P3 and P20 means passages 3 and 20
2. **P1 + 18 + 1 S to TCS indicates that cells were cultured at TCS for 1 passage and transferred to polysaccharide medium (S) for 18 passages, and then transferred back to TCS for 1 passage.
3. ***P1 + 18 + 1 C to TCS indicates that cells were cultured at TCS for 1 passage and transferred to polysaccharide coated surface (C) for 18 passages, and then transferred back to TCS for 1 passage.

Figure 6A:
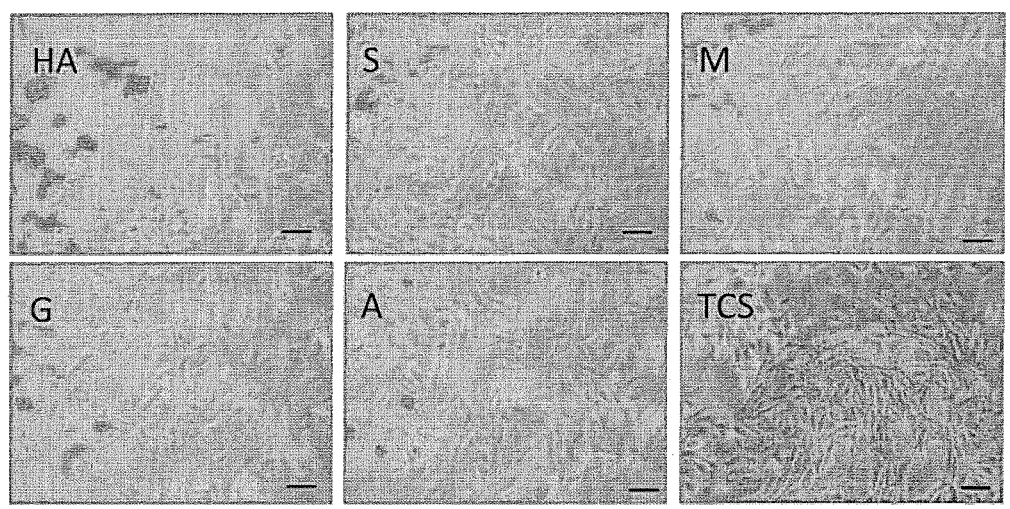
FIG. 6A illustrates the maintenance of proliferation and differentiation potentials of the indicated fibroblast cells preconditioned on the various surfaces or various media as hyaluronan (HA), chondroitin sulfate (S), carboxymethyl cellulose (M), carrageenan (G), and alginate (A); tissue cultural surface (TCS) referred as to control group, and scale bar is 100 μm.
Figure 6B:
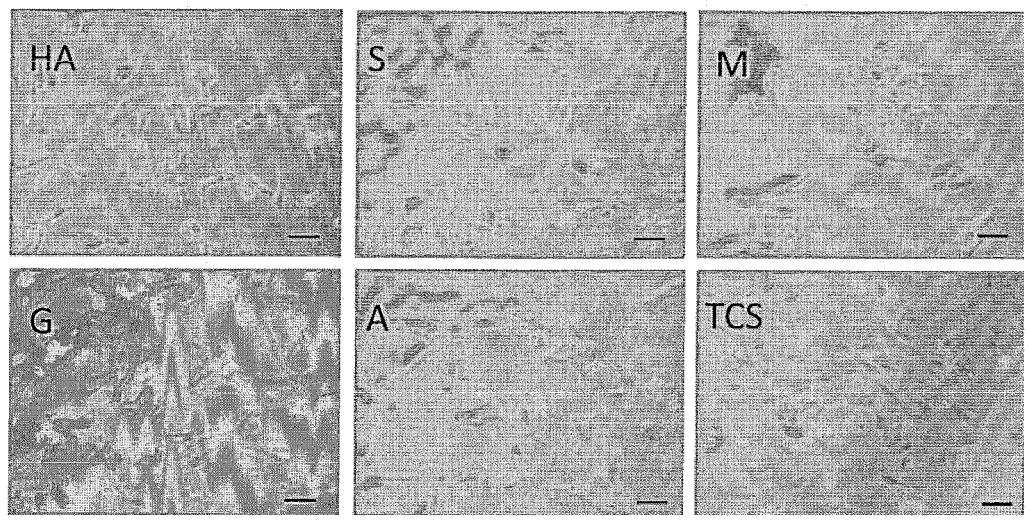
FIG. 6B illustrates the maintenance of proliferation and differentiation potentials of the indicated placenta derived mesenchymal stem cells (PDMSC) preconditioned on the various surfaces or various media as hyaluronan (HA), chondroitin sulfate (S), carboxymethyl cellulose (M), carrageenan (G), and alginate (A); tissue cultural surface (TCS) referred as to control group, and scale bar is 100 μm.
Figure 7:
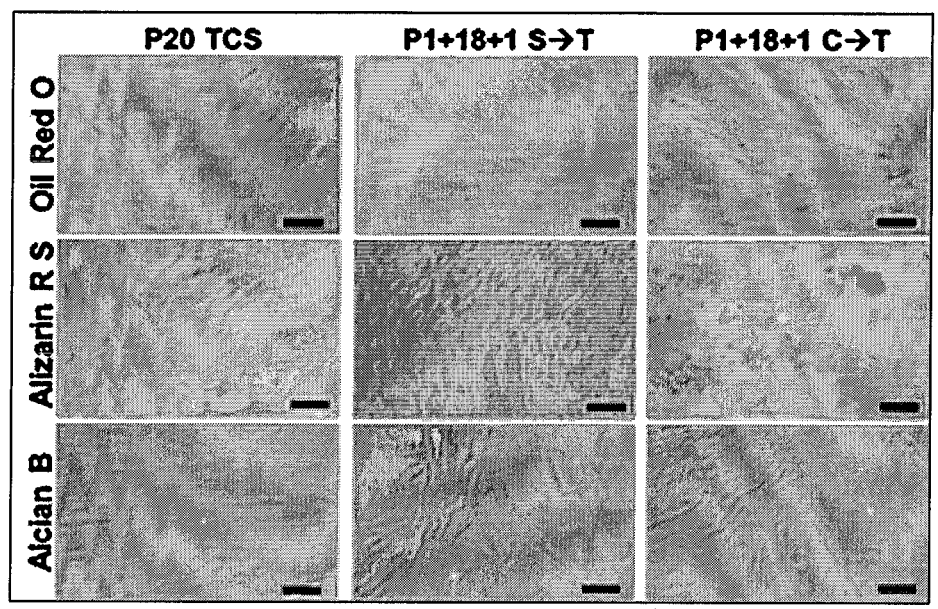
FIG. 7 illustrates the differentiation potentials of cells cultured at indicated conditions such as adipogenesis, osteogenesis, chondrogenesis.

As shown in FIGS. 6A and 6B, Table 1 and Table 2, it was observed that the proliferation and differentiation potentials of the cells were preserved after pre-treatment at the indicated conditions. The proliferative rates largely increased after transferred the cells to regular tissue cultural surface for a long period of time in comparison to the control group. So as the differentiation potentials of the cells.

CONCLUSION

Regarding mADSCs, the applicant investigated the effects of CHA on mADSCs and observed the formation of cell aggregates with a much more gradual growth profile during entire culture period. The transferring cultures (CHA_P3/C and CHA_P5/C) were carried out, and mADSCs on CHA_P3/C demonstrated a further prolongation of cultural lifespan, while mADSCs on CHA_P5/C demonstrated a possible dormant state of mADSCs being stimulated with incubation with CHA. Both of the conditions can act to preserve the proliferative and differentiation potentials of mADSCs.

Regarding hPDMSCs, the applicant demonstrated here that CHA reduced the proliferation of hPDMSCs, but did not hamper the proliferative activity of hPDMSCs, even in long-term serial passage. The results of this research showed that HA could be a promising candidate to serve as the cultural substratum for MSCs for keeping them at slow-cycling status in vitro.

In addition, the applicant also investigated effects of proteinaceous ECM components for comparison with polysaccharide and their derivatives. The proliferative rate of hADSCs on a HA-coated culture surface was compared with the proliferative rate of hADSCs on a collagen-coated culture surface. The results showed that the proliferative rate of hADSCs on the collagen-coated culture surface was faster than that on the HA-coated culture surface (data not shown). The results further demonstrated that the proteinaceous ECM component such as collagen promoted rather than preserved proliferation and differentiation of the hADSCs, which agreed with what has been reported in WO 2008/007082 A2.

HA can be prepared from either animal tissues or plant tissues or by genetic engineering. On the contrary, collagen is difficult to be vastly produced by genetic engineering if there is disease transmission concern from animal sources. This is because that the tropocollagen gene is extremely long and a native collagen molecule contains three correctly intertwisted strands which is difficult to be achieved by genetic engineering technique nowadays. Compared to collagen, the industrial techniques for preparing polysaccharide including HA have been well established. Therefore, using the polysaccharide obtained from resources other than animals or by genetic engineering in accordance with the present invention to preserve proliferation and differentiation potential of undifferentiated cells can cause less disease transmission problems.

In conclusions, the introduction of HA in a culture system is capable of being used for expanding undifferentiated cells such as mesenchymal cells in vitro without loss of their replicative ability and differentiation capacity. The present invention provides methods for preserving proliferation and differentiation potential of undifferentiated cells with immobilized non-proteinaceous ECM components that are valuable for the applications in regenerative medicine and tissue engineering.

All patents, patent applications, and literature cited in the specification were incorporated by reference in their entirety. In the case of any inconsistencies, the present disclosure, including any definitions therein will prevail.

Even though numerous characteristics and advantages of the present invention have been set forth in the foregoing description, together with details of the structure and features of the invention, the disclosure is illustrative only. Changes may be made in the details within the principles of the invention to the full extent indicated by the broad general meaning of the terms in which the appended claims are expressed.

What is claimed is:

1. A method for preserving proliferation and differentiation potential of undifferentiated cells, comprising steps of:
   providing a culture carrier having a surface coated with a biological material selected from the group consisting of hyaluronan, chondroitin sulfate, carboxymethyl cellulose, carrageenan, alginate, and chitosan; and
   inoculating and culturing the undifferentiated cells on the surface in the culture carrier with an appropriate medium, such that the proliferation and differentiation potential of the undifferentiated cells are preserved, wherein the undifferentiated cells are selected from the group consisting of mesenchymal stem cells, tissue progenitor cells and mesenchymal cells.

2. The method according to claim 1, wherein the mesenchymal stem cells are selected from the group consisting of adipose-derived stromal cells, adipose-derived mesenchymal stem cells, placenta-derived mesenchymal stems cells and bone marrow-derived mesenchymal stem cells.

3. The method according to claim 1, wherein the concentration of the biological materials is an amount from 1 µg/cm$^2$ to 200 µg/cm$^2$.

4. The method according to claim 3, wherein the concentration of the biological materials is the amount from 5 µg/cm$^2$ to 100 µg/cm$^2$.

5. The method according to claim 4, wherein the surface is coated with the biological materials is 30 µg/cm$^2$.

6. The method according to claim 1 further comprising subculturing the undifferentiated cells in a second culture carrier.

7. The method according to claim 6, wherein the second culture carrier has a surface coated with the biological material and the undifferentiated cells are cultured thereon.

8. The method according to claim 1, wherein the biological material has an average molecular weight in a range from 1 KDa to 20,000 KDa.

9. The method according to claim 8, wherein the biological material has an average molecular weight in a range from 10 KDa to 15,000 KDa.

10. The method according to claim 1, wherein the appropriate medium comprises polysaccharides or sulfated polysaccharides.

11. The method according to claim 10, wherein the polysaccharides or sulfated polysaccharides is selected from the group consisting of hyaluronan, chondroitin sulfate, carboxymethyl cellulose, carrageenan, alginate, and chitosan.

12. The method according to claim 10, wherein the polysaccharides or sulfated polysaccharides are amount from 0.001 mg/ml to 100 mg/ml.

* * * * *